United States Patent
Levin et al.

(10) Patent No.: US 12,006,237 B2
(45) Date of Patent: Jun. 11, 2024

(54) EFFICIENT OPERATION OF AN ANAEROBIC-AEROBIC SBR

(71) Applicant: S.G.T.—SUSTAINABLE GREEN TECHNOLOGIES LTD, Netanya (IL)

(72) Inventors: Gal Levin, Netanya (IL); Reuven Eitan, Giv'at Shmuel (IL)

(73) Assignee: S.G.T.—SUSTAINABLE GREEN TECHNOLOGIES LTD, Netanya (IL)

( * ) Notice: Subject to any disclaimer, the term of this patent is extended or adjusted under 35 U.S.C. 154(b) by 618 days.

(21) Appl. No.: 17/273,861

(22) PCT Filed: Sep. 15, 2019

(86) PCT No.: PCT/IL2019/051028
§ 371 (c)(1),
(2) Date: Mar. 5, 2021

(87) PCT Pub. No.: WO2020/058970
PCT Pub. Date: Mar. 26, 2020

(65) Prior Publication Data
US 2021/0347664 A1   Nov. 11, 2021

(30) Foreign Application Priority Data
Sep. 17, 2018   (IL) .......................................... 261842

(51) Int. Cl.
*C02F 1/00*   (2023.01)
*C02F 3/12*   (2023.01)
(Continued)

(52) U.S. Cl.
CPC .............. *C02F 11/02* (2013.01); *C02F 1/008* (2013.01); *C02F 3/1263* (2013.01); *C02F 3/282* (2013.01);
(Continued)

(58) Field of Classification Search
CPC ........ C02F 3/1263; C02F 3/282; C02F 11/02; C02F 2209/03; C02F 2301/06
See application file for complete search history.

(56) References Cited

U.S. PATENT DOCUMENTS

| | | | |
|---|---|---|---|
| 4,919,815 A | 4/1990 | Copa et al. | |
| 5,792,355 A | 8/1998 | Desjardins | |

(Continued)

FOREIGN PATENT DOCUMENTS

| | | |
|---|---|---|
| CN | 1548390 A | 11/2004 |
| CN | 1622921 A | 6/2005 |

(Continued)

OTHER PUBLICATIONS

Chang, Han Jung—KR100460942 B1 machine translation—Jun. 2, 2004 (Year: 2004).*

(Continued)

*Primary Examiner* — Bradley R Spies
(74) *Attorney, Agent, or Firm* — Hoffman Warnick LLC

(57) ABSTRACT

A method for the efficient operation of a waste treatment apparatus comprising an anaerobic-aerobic sequencing batch reactors (SBR). The method comprises the synchronized transfer of waste between the reactors, for preventing unsafe buildup of pressure in the anaerobic reactor and reaching unsafe levels.

4 Claims, 1 Drawing Sheet

(51) Int. Cl.
  *C02F 3/28*    (2023.01)
  *C02F 3/30*    (2023.01)
  *C02F 11/02*   (2006.01)
  *C02F 103/22*  (2006.01)
  *C02F 103/32*  (2006.01)

(52) U.S. Cl.
  CPC .......... *C02F 3/305* (2013.01); *C02F 2103/22* (2013.01); *C02F 2103/32* (2013.01); *C02F 2209/03* (2013.01); *C02F 2301/046* (2013.01); *C02F 2301/06* (2013.01)

(56) References Cited

U.S. PATENT DOCUMENTS

| | | | |
|---|---|---|---|
| 6,126,827 | A | 10/2000 | Johnson, Jr. et al. |
| 6,190,554 | B1 | 2/2001 | Mandt |
| 6,398,957 | B1 | 6/2002 | Mandt |
| 6,444,124 | B1 | 9/2002 | Onyeche et al. |
| 6,676,836 | B2 | 1/2004 | Mandt |
| 7,163,629 | B2 | 1/2007 | Abu-Orf et al. |
| 2002/0074287 | A1 | 6/2002 | Park et al. |
| 2002/0079266 | A1 | 6/2002 | Ainsworth et al. |
| 2002/0185448 | A1 | 12/2002 | Chisholm et al. |
| 2005/0035059 | A1 | 2/2005 | Zhang et al. |
| 2005/0087480 | A1 | 4/2005 | Park et al. |
| 2005/0189295 | A1 | 9/2005 | Barnard |
| 2011/0089105 | A1 | 4/2011 | Liu et al. |
| 2011/0203992 | A1 | 8/2011 | Liu et al. |
| 2012/0006745 | A1 | 1/2012 | Kaley et al. |
| 2018/0186672 | A1 | 7/2018 | Levin |

FOREIGN PATENT DOCUMENTS

| | | |
|---|---|---|
| CN | 101602541 A | 12/2009 |
| CN | 101723538 A | 6/2010 |
| CN | 102060413 A | 5/2011 |
| CN | 102583931 A | 7/2012 |
| CN | 102583933 A | 7/2012 |
| CN | 204369650 U | 6/2015 |
| CN | 105668946 A | 6/2016 |
| CN | 107381812 A | 11/2017 |
| JP | H1043790 A | 2/1998 |
| JP | 2004290826 A | 10/2004 |
| KR | 20020087799 A | 11/2002 |
| KR | 100460942 B1 | 12/2004 |
| KR | 101338772 B1 | 12/2013 |
| WO | 2006019256 A1 | 2/2006 |
| WO | 2011066866 A1 | 6/2011 |
| WO | 2011106621 A2 | 9/2011 |
| WO | 2012019310 A1 | 2/2012 |
| WO | 2017218239 A1 | 12/2017 |
| WO | 2018106986 A1 | 6/2018 |

OTHER PUBLICATIONS

Chan Y. J. et al. "A review on anaerobic-aerobic treatment of industrial and municipal wastewater" Chemical Engineering Journal, vol. 155, No. 1-2, pp. 1-18, Dec. 2009.

Engineering technology examples and supporting technical product equipment, pollution control department of the State Environmental Protection Administration, Figure 1 on p. 52-the penultimate paragraph on p. 53, China Environmental Science Press, May 31, 2004.

Hala El-Kamah et al., "Treatment of high strength wastewater from fruit juice industry using integrated anaerobic/aerobic system," Elsevier, ScienceDirect, Desalination, 253, 2010, pp. 158-163.

Zhang R et al., "Treatment of Swine Wastewater with biological conversion, filtration, and reverse osmosis: A laboratory study, Transactions of the ASAE", 2004, vol. 47, No. 1, pp. 243-250.

Chinese Office Action for Application No. 201980069011.6, dated Jul. 25, 2022, 13 pages.

Indian Office Action for Application No. 202137010869, dated Jun. 21, 2022, 7 pages.

Extended European Search Report for Application No. 19863402.4, dated May 2, 2022, 9 pages.

PCT International Search Report and Written Opinion for International Application No. PCT/IL2019/051028, dated Dec. 16, 2019, 11 pages.

\* cited by examiner

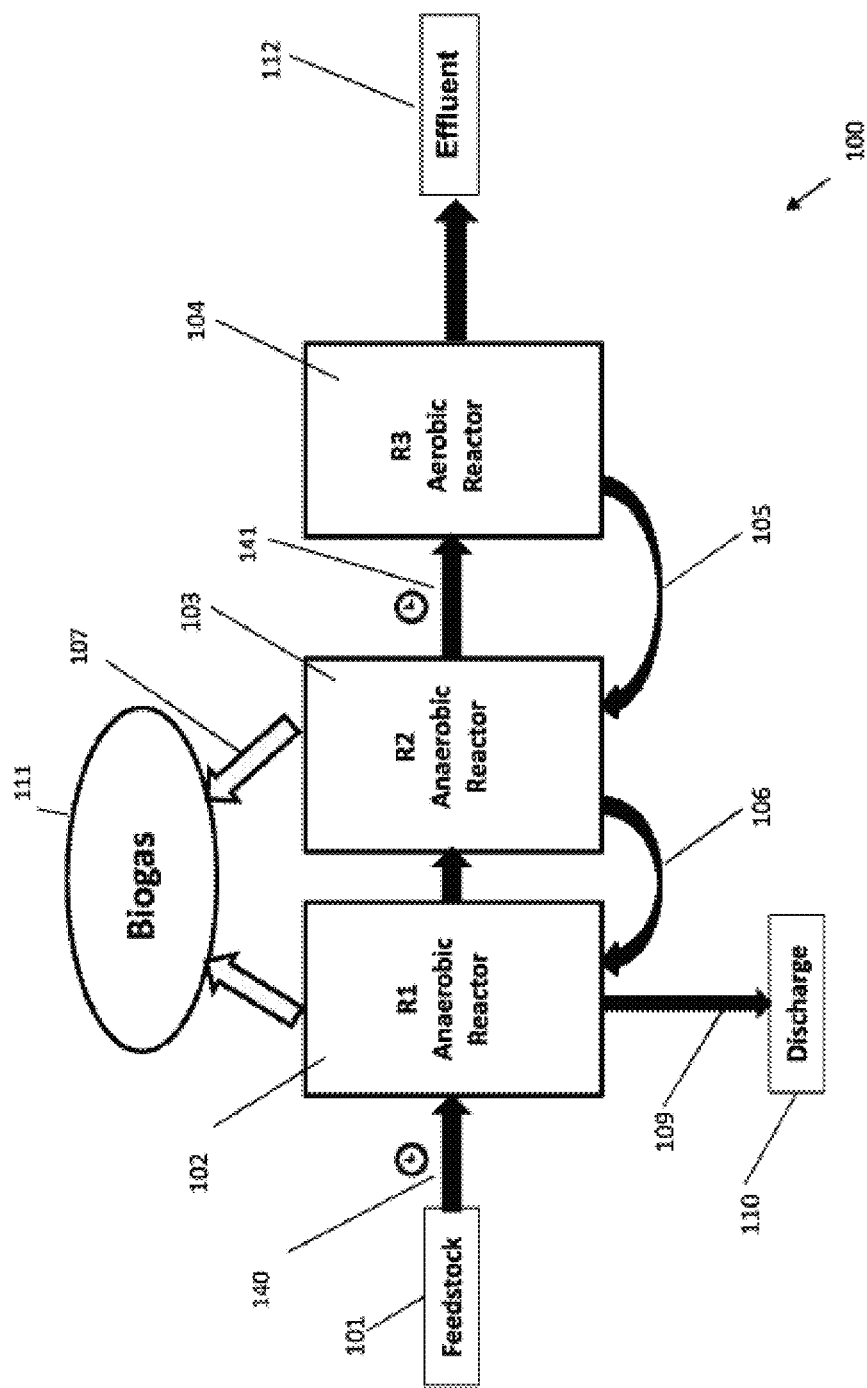

EFFICIENT OPERATION OF AN ANAEROBIC-AEROBIC SBR

FIELD OF THE INVENTION

The present invention relates to a method for the efficient operation of a waste treatment apparatus comprising anaerobic-aerobic sequencing batch reactors (SBR). More particularly, the method comprises the synchronized transfer of waste between the reactors of the apparatus.

BACKGROUND OF THE INVENTION

Anaerobic digestion (AD) is a biological process that breaks down organic materials (feedstocks) in the absence of oxygen (anaerobic conditions) into biogas, containing mainly methane ($CH_4$) and carbon dioxide ($CO_2$). An anaerobic-aerobic sequencing batch reactor (SBR) apparatus comprises both an anaerobic and an aerobic reactor, where the influent of the aerobic reactor is pretreated in the anaerobic reactor. In an SBR the amount of daily waste is treated in batches. Anaerobic-aerobic sequencing batch reactor (SBR) apparatus is an arrangement well known in the art, in which anaerobic and aerobic batch reactors are operated.

Feedstock waste is first fed to the anaerobic reactor and then the treated waste is transferred from the anaerobic reactor to the aerobic reactor. The anaerobic reactor comprises a gas collector for collection of biogas produced during breakdown of feedstock in the reactor.

The biogas produced during anaerobic digestion causes pressure to build up in the anaerobic reactor. The reactor's capacity for waste and biogas is limited by the size of the reactor. It has now been found that in order to effectively operate a plurality of reactors of the type described above, it is advantageous to perform a regulated transfer of waste between the reactors. Such transfer of wastes results in an efficient operation of the system, as well as preventing pressure from building up within the anaerobic reactor and reaching unsafe levels.

According to the present invention the feeding of waste into the facility is synchronized with the transfer of waste from the anaerobic reactor to the aerobic reactor in a an anaerobic-aerobic SBR apparatus.

The above and other purposes and advantages of the invention will become apparent as the description proceeds.

SUMMARY OF THE INVENTION

The present invention advantageously provides a method for preventing unsafe buildup of pressure in pressure in at least one anaerobic reactor a system comprising an anaerobic-aerobic sequencing batch reactor (SBR) arrangement, comprising at least one anaerobic reactor and one aerobic reactor, while avoiding vacuum in the second anaerobic reactor each of these reactors being in recycling communication with at least one other reactor, comprising the steps of: i) feeding a feedstock waste to said at least one anaerobic reactor; and simultaneously, ii) transferring the same portion of waste from said at least one anaerobic reactor to said aerobic reactor.

In some embodiments, the method further comprises iii) transferring a portion of waste activated sludge (WAS) from said aerobic reactor to said at least one anaerobic reactor; and simultaneously, iv) discharging a portion of WAS from said at least one anaerobic reactor.

BRIEF DESCRIPTION OF THE DRAWINGS

In the drawings:

FIG. 1 is a schematic representation of an apparatus operating according to the invention.

DETAILED DESCRIPTION

In one embodiment, the present invention operates in an anaerobic-aerobic sequencing batch reactor (SBR) apparatus having at least one anaerobic reactor and an aerobic reactor, in recycling communication, and comprises the steps of:
   i) feeding feedstock waste to the at least one anaerobic reactor; and simultaneously,
   ii) transferring waste from the at least one anaerobic reactor to the aerobic reactor.

One of the advantages achieved by the invention is that of preventing unsafe buildup of pressure in the at least one anaerobic reactor while avoiding vacuum in the second anaerobic reactor. The regulation of pressure allows efficient and constant operation of the apparatus which allows the denitrification to reach peak rate in the SBR. The denitrification occurs simultaneously with the peak rate of the decomposition of organic matter in the Anaerobic SBR.

As used herein, the term "feedstock" refers to organic material to be treated. In some embodiments, the feedstock may be sewage sludge, livestock waste, food and drink waste, including slaughterhouse, bakery or brewery waste, and agricultural waste, but the invention is not limited to any specific feed material.

As used herein, the term "recycling communication" is used to indicate that the liquid, waste, sludge or gas may be recycled from one component of the facility to another, i.e. the waste is transferred between components of the facility. The term also encompasses transfer of portions of waste. Accordingly, it should be understood that a reactor is considered to be found in recycling communication with another reactor if it either transfers waste from itself to another reactor, or receives waste transferred to it from another reactor, even though it may not transfer waste to another reactor.

It will be appreciated by the skilled person, that in some embodiments, where the apparatus comprises more than one anaerobic reactor, the anaerobic reactors are in recycling communication with one another such that the pressure is uniform, or alternatively, that the simultaneous transfer of waste is linked between these reactors.

According to some embodiments, the invention may be applied to an anaerobic-aerobic SBR apparatus such as the one schematically depicted in FIG. 1. The apparatus 100 comprises two anaerobic reactors 102, 103 and an aerobic reactor 104. Feedstock waste 101 is fed via line 140 in batches into the first anaerobic reactor 102. Simultaneously, waste is transferred via line 141 in batches from the second anaerobic reactor 103 to the aerobic reactor 104. The apparatus comprises a discharge vessel 110 and an effluent vessel 112 and conduits such as 140, 141, 105, 106 to facilitate the flow of waste through the reactors of the apparatus. In some embodiments, biogas 111 may be collected from the anaerobic reactors 102, 103 via 107.

In some embodiments waste is transferred via line 105 from the aerobic reactor 104 to the second anaerobic reactor 103 and simultaneously, a bottom portion of waste is discharged via line 109 from the first anaerobic reactor 102.

As used herein, the term "waste" refers to material that can be drawn from the bottom portion of a reactor. In this respect, the bottom portion will normally be considered the bottom third of the reactor, but the withdrawal point can be located at various heights and positions in the reactor, and is not limited to any particular location.

The present invention is applicable to any anaerobic-aerobic sequencing batch reactor (SBR) apparatus, which may comprise one or more anaerobic reactors, at least one aerobic reactor and any number of reserve and treatment tanks or vessels. Such tanks may be, but are not limited to, water tanks for containing the water effluent, collection tanks for containing feedstock to be fed to the apparatus, tanks for containing the discharged waste or tanks for further treatment and purification of the water effluent.

Illustrative and non-limitative examples of anaerobic reactors suitable for operation in the context of the invention is an anaerobic sequencing batch reactor (ASBR). The anaerobic reactor may comprise a gas collector for collecting biogas, including methane.

Illustrative and non-limitative examples of aerobic reactors suitable for operation in the context of the invention is a sequencing batch reactor (SBR). The aerobic reactor may comprise an aeration device for supplying air or oxygen to the reactor.

The reactors are in communication with one another through a conduit, channel, pipe or tube suitable for transferring liquid, waste, sludge or gas from one component of the facility to another. Pumps and gravity driven means can be included in a conduit, conduit, channel, pipe or tube to facilitate transfer of liquid, waste, sludge or gas. In some cases, the conduit, channel, pipe or tube may further comprise valves capable of opening and closing for regulating the flow of waste.

In some embodiments, the method further comprises:
iii) transferring a portion of waste activated sludge (WAS), as defined hereinafter, from said aerobic reactor to said at least one anaerobic reactor; and simultaneously,
iv) discharging a portion of waste activated sludge (WAS) from said at least one anaerobic reactor.

As used herein, the term "portion" denotes a volume of waste or sludge which is determined according to the size of the reactors in the apparatus. Accordingly, it will be appreciated by the skilled person that the volume of said portion is scalable and is set according to the capacity of the facility and other considerations. The volume of said portion may also vary according to the components of the facility from which and to which the portion is being transferred.

As used herein, the term "waste activated sludge" or "WAS" relates to settled solids at the bottom portion of the reactor, containing particles and living organisms. Said WAS may occupy different heights of the bottom portion of the reactor, and will typically form a sludge that is flowable.

As will be appreciated by the skilled person, one of the advantages of the invention is that it provides a simple method for pressure adjustment in an anaerobic-aerobic SBR apparatus for preventing unsafe buildup of pressure in the anaerobic reactor, thus affording safer and more easily equalized operation of the system.

Although exemplary embodiments of the invention have been described, it will be understood that the invention may be carried out with many variations, modifications, and adaptations, without exceeding the scope of the claims.

The invention claimed is:

1. A method for preventing unsafe buildup of pressure in pressure in at least one anaerobic reactor in a system comprising two anaerobic reactors in recycling communication with one another and at least one aerobic reactor in sequencing batch reactor (SBR) arrangement, while avoiding vacuum in a second one of said anaerobic reactors, each of said reactors being in recycling communication with at least one other reactor, comprising the steps of:
   i) feeding a feedstock waste of a specified volume to a first anaerobic reactor; and simultaneously,
   ii) transferring a portion of waste of said specified volume from said second anaerobic reactor to said aerobic reactor.

2. The method of claim 1, further comprising:
iii) transferring a portion of waste activated sludge (WAS) having said specified volume from said aerobic reactor to said second anaerobic reactor; and simultaneously,
iv) discharging a portion of WAS having said specified volume from said second anaerobic reactor.

3. The method of claim 1, further comprising:
transferring waste from said second anaerobic reactor to said first anaerobic reactor.

4. The method of claim 1, further comprising:
transferring waste from said aerobic reactor to said second anaerobic reactor.

* * * * *